United States Patent [19]

Sunshine et al.

[11] Patent Number: 4,975,426

[45] Date of Patent: Dec. 4, 1990

[54] COUGH/COLD MIXTURES COMPRISING NON-SEDATING ANTIHISTAMINE DRUGS

[75] Inventors: Abraham Sunshine, New York; Eugene M. Laska, Larchmont; Carole E. Siegel, Mamaroneck, all of N.Y.

[73] Assignee: Analgesic Associates, Larchmont, N.Y.

[21] Appl. No.: 315,161

[22] Filed: Feb. 24, 1989

Related U.S. Application Data

[62] Division of Ser. No. 59,635, Jun. 8, 1987, Pat. No. 4,829,064.

[51] Int. Cl.$^5$ .................. A61K 31/60; A61K 31/62; A61K 31/615; A61K 31/505; A61K 31/44; A61K 31/445; A61K 31/19

[52] U.S. Cl. .................. 514/159; 514/161; 514/165; 514/166; 514/256; 514/290; 514/315; 514/336; 514/570

[58] Field of Search .......... 514/159, 165, 256, 290, 514/315, 336, 570, 629, 630

[56] References Cited

PUBLICATIONS

Handbook of Nonprescription Drugs 8th ed, (1986) pp. 137-139 and 166.
The Merck Index 10th ed (1983), pp. 1310-1311 and APP-1.
Chemical Abstracts 104(1):517, Cohen et al. (1986).
Chemical Abstracts 106(5):27517t, Roman et al. (1986).
Chemical Abstracts, 106(15):113384d, Calcutt et al. (4/13/87).

*Primary Examiner*—Douglas W. Robinson
*Assistant Examiner*—Raymond J. Henley, III
*Attorney, Agent, or Firm*—Burns, Doane, Swecker & Mathis

[57] ABSTRACT

Pharmaceutical compositions and methods of using same comprising aspirin, sodium salicylate, salicylamide or acetaminophen, in combination with a non-sedating antihistamine and optionally one or more other active components selected from a decongestant, cough suppressant (antitussive) or expectorant are provided for the relief of cough, cold, cold-like and/or flu symptoms and the discomfort, pain, headache, fever and general malaise associated therewith.

33 Claims, No Drawings

COUGH/COLD MIXTURES COMPRISING NON-SEDATING ANTIHISTAMINE DRUGS

This application is a division of application Ser. No. 059,635, filed Jun. 8, 1987, now U.S. Pat. No. 4,829,064.

Appicants have filed a number of applications concerning cough/cold formulations containing the newer non-steroidal anti-inflammatory drugs. These applications which are assigned to Richardson-Vicks, Inc. include U.S. Ser. No. 042,120, filed Apr. 24, 1987, now U.S. Pat. No. 4,783,465 which is a continuation-in-part of U.S. Ser. No. 887,205, filed Jul. 21, 1986, now U.S. Pat. No. 4,738,966 and U.S. Ser. Nos. 016,333, 016,344, 016,376, 016,377, 016,397 and 016,563 all of which were filed Feb. 19, 1987 and are now U.S. Pat. Nos 4,749,697, 4,749,722, 4,749,711, 4,749,720 and 4,749,712, which are divisional applications of U.S. Ser. No. 887,205, filed Jul. 21, 1986, which is a divisional of U.S. Ser. No. 702,546, filed Jul. 8, 1985, now U.S. Pat. No. 4,619,934, which is a divisional of U.S. Ser. No. 598,502, filed Apr. 9, 1984, now U.S. Pat. No. 4,522,899.

BACKGROUND OF THE INVENTION

The present invention relates generally to novel pharmaceutical compositions of matter comprising aspirin, sodium salicylate, salicylamide or acetaminophen, in combination with a non-sedating antihistamine and optionally one or more other active components selected from a sympathomimetic drug (e.g. nasal decongestant or bronchodilator), cough suppressant and/or expectorant, optionally in combination with suitable pharmaceutically acceptable non-toxic carriers or excipients, and to methods of using said compositions in the treatment, management or mitrigation of cough, cold, cold/-like and/or flu symptoms and the discomfort, pain, headache, fever and general malaise associated therewith.

Aspirin, salicylamide and acetaminophen have heretofore been included as the pain reliever and fever-reducing component in conventional cough/cold multisymptom alleviating compositions.

Exemplary prior art cough/cold formulations containing aspirin, salicylamide or acetaminophen include Corincidin®, Coricidin D®, Comtrex®, Dristan®, Daycare®, Cotylenol®, Sinubid® and the like. These formulations generally contain in addition to aspirin, salicylamide or acetaminophen, one or more conventional antihistaminics, decongestants, cough suppressants, antitussives and expectorants.

One of Applicants' earlier applications, U.S. Pat. No. 4,619,934, was directed to one or more of the newer non-steroidal anti-inflammatory (NSAIDs) drugs (specifically excluding aspirin, acetaminophen and the like) in combination with a conventinal antihistamine and optionally other cough/cold components. Subsequently, Applicants filed U.S. Ser. No. 042,120 on Apr. 24, 1987 which covers the non-sedating antihistamines, which are pharmacologically and chemically distinct from the conventional antihistamines, in combination with the newer NSAIDs. That combination offers significant advantages in the treatment, management or mitigation of cough, cold, cold-like and/or flu symptoms and the discomfort, pain, headache, fever and general malaise associated therewith.

It is well known that the conventional antihistamines may cause drowsiness or marked drowsiness. While this may be an advantage at bedtime, if taken during the day, the label recommends that a patient use caution when driving a motor vehicle or operating machinery. Therefore, the combination of a non-sedating antihistamine and the newer NSAIDs is therefore particularly advantageous for daytime administration.

However, because of individual variability there are many patients for whom the newer NSAIDs do not perform as effectively or produce more side effects in comparison with aspirin, sodium salicylate, salicylamide or acetaminophen.

It has not heretofore been proposed to use aspirin, sodium salicylate, salicylamide or acetaminophen along with a non-sedating antihistamine in the preparation of advantageous cough-cold pharmaceutical compositions. Such combinations are particularly advantageous for daytime use by patients for whom the newer NSAIDs offer little or no benefit.

SUMMARY OF THE INVENTION

It is, therefore, a primary object of the present invention to provide pharmaceutical compositions of matter comprising an analgesically effective amount of aspirin, sodium salicylate, salicylamide or acetaminophen, in combination with a non-sedating antihistamine, and optionally one or more active components selected from a decongestant, cough suppressant, expectorant and, further optionally including pharmaceutically acceptable carriers therefor.

It is a further object of the present invention to provide methods for the symptomatic relief of cough, cold, cold-like and flu symptoms and the discomfort, pain, headache, fever and general malaise associated therewith, by the administration of preselected dosages of the pharmaceutical compositions of the present invention. Cold-like symptoms as used herein refers to coryza, nasal congestion, upper respiratory infections, allergic rhinitis, otitis, sinusitis, etc.

Another object of the present invention is to provide suitable dosage unit forms of aspirin, sodium salicylate, salicylamide or acetaminophen, in combination with a non-sedating antihistamine and optionally one or more active components selected from a decongestant, cough suppressant or expectorant adapted for convenient oral administration.

DETAILED DESCRIPTION OF THE INVENTION

The analgesic and anti-inflammatory components in the cough-cold compositions of the present invention include the salicylic acid derivatives and acetaminophen. The salicylic acid derivatives include aspirin, sodium salicylate and salicylamide. The individual dosages for the analgesic and anti-inflammatory components of the present invention may range from about 300 mg to 2.0 grams. However, greater or lesser amounts may be employed if desired or necessary. The frequency of adminstration may range anywhere from three to twelve hours.

Aspirin is known by a variety of chemical names, including 2-(acetyloxy)-benzioc acid, acetylasalicylic acid or salicylic acid acetate. The chemical structure for aspirin is set forth below:

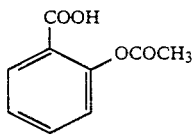

In the past, aspirin has generally been considered to be the drug of choice when a mild analgesic is indicated. Aspirin has been found to be more useful in the treatment of headache, neuralgia, myalgia, arthralgia, and other pain arising from ontegumental structures than in acute severe pain of visceral origin. It has been used to relieve moderate postoperative and postpartum pain and other visceral pain, such as that secondary to trauma or cancer. When therapy is indicated to reduce fever, aspirin is one of the most effective drugs. Aspirin has an anti-inflammatory action in large doses, which may contribute to relief of pain when inflammation is a factor. This drug is one of the primary agents in the management of some rheumatic diseases.

The dosage for aspirin, as well as the other salicylic acid derivatives and acetaminophen, should be individualized depending on the type and severity of the symptoms. The patient's weight, age and renal function should also be taken into consideration. The usual adult dosage range useful in the practice of the present invention is from about 300 mg to 1 gram every four to twelve hours. Generally, a dosage of about 500 mg every four to eight hours is administered. In adults, the "extra strength" dosage 1.0 gram every four to eight hours is common. A dosage for children is approximately 11 mg/kg every four hours or 16 mg/kg four every six hours, with a maximum daily dose of 3.6 grams.

Another salicylic acid derivative, sodium salicylate, has the chemical structure:

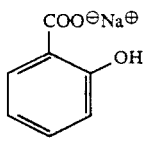

Sodium salicylate is also known as the monosodium salt of 2-hydroxybenzoic acid or monosodium salicylate. As is the case with aspirin, sodium salicylate is widely employed for the relief of pain and the reduction of fever. Sodium salicylate is about ⅓ less potent, on a weight basis, than aspirin, and therefore the equivalent analgesic dose is somewhat higher. The sodium salt tends to cause gastric irritation due to the liberation of free salicylic acid by the acid gatric juice. For this reason, an equivalent amount of sodium bicarbonate is sometimes employed along with sodium salicylate. In the practice of the present invention, the dosage range is from about 300 mg to 2 grams every four to six hours. The usual adult dosage is about 600 mg every four to six hours.

The other salicylic acid derivative, salicylamide, has the chemical structure:

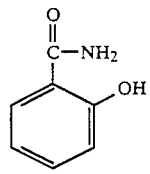

Unlike aspirin, salicylamide is stable in liquid formulations, does not produce gastric damage and can be taken by persons allergic to salicylates. Clinical studies indicate that salicylamide's analgesic potency, antipyretic and anti-inflammatory properties are similar to, but less than, those for aspirin. The dose of salicylamide for use in the practice of the present invention can range from about 300 mg to 2 grams every three to four hours. The usual dosage is from about 300 mg to 600 mg every three to four hours.

Acetaminophen is also know as N-(4-hydroxyphenyl)-aceamide, N-acetyl-p-aminophenol (APAP), p-acetamidophenol or 4'-hydroxyacetanilide and has the following chemical structure:

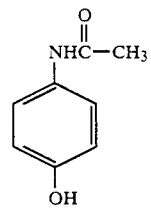

On a milligram for milligram basis the efficacy of acetaminophen as an analgesic and antipyretic is widely believed to be equivalent to that of aspirin. It is used to treat headache, mild to moderate myalgia, arthralgia, chromic pain from cancer, postpartum pain, postoperative pain, and fever. It is the preferred alternative analgesicantipyretic to aspirin and the newer NSAIDs, particularly in patients who cannot tolerate aspirin, those with a coagulation disorder (e.g., hemophilia), or individuals with a history of peptic ulcer. Unlike aspirin, acetaminophen does not antagonize the effects of uricosuric agents; thus, it may be used in patients with gouty arthritis who are taking a uricosuric. Moreover, epidemiological evidence has suggested the possibility of an association between the use of aspirin in the treatment of fever in children with varicella (chickenpox) or influenza virus infections and the subsequent development of Reye's syndrome. Thus, acetaminophen is the drum of choice for such patients.

For use in the practice of the present invention the adult dosage ranges from about 325 mg to 4.0 grams daily. The preferred adult dosage is from about 325 to 1000 mg four to six times daily as necessary. For children the usual dosage range is 20 mg to 300 mg every four hours depending on body weight.

Aspirin and acetaminophen are the preferred analgesic and antipyretic components useful in combination with the non-sedating antihistamines in the cough/cold compositions of the present invention.

The non-sedating antihistamines are pharmacologically and chemically distinct from the conventional antihistamines. The non-sedating antihistamines represent a new generation of drugs which specifically block $H_1$-histamine receptors and do not cause sedation. The sedative properties of conventional antihistamines are well known and for daytime use especially represent a significant disadvatage during treatment. The FDA's Tentative Final Monograph has proposed that the labeling for category I OTC conventional antihistamines, in general, carry the warning, "May cause drowsiness; alcohol may increase the drowsiness effect. Avoid alcoholic beverages while taking this product. Use caution while driving a motor vehicle or operating machinery." The non-sedating antihistamines are only peripherally active. That is, they do not penetrate the blood-brain barrier in significant amounts to cause drowsiness. Thus, unlike the conventional antihistamines, the labeling for the non-sedating antihistamines do the carry warnings to patients to refrain from driving a car or operating machinery during therapy or concomitantly using alcohol or other central nervous system depressants as they do for conventional antihistamines. Nor are the non-sedating antihistamines contradinducted in patients who are suffering from glaucoma, bronchial asthma, or prostatic hypertrophy.

In vivo studies have shown that the non-sedating antihistamines preferentially bind to peripheral rather than central $H_1$-histamine receptors. Since conventional antihistamines which produce sedation have greater affinities for central $H_1$-histamine receptors, the lesser penetration of the non-sedating antihistamines into the central nervous system may be responsible for their apparent lack of central nervous system effects. In addition, as a general rule, the non-sedating antihistamines possess minimal or no antiserotoninergic, anticholinergic or antiadrenergic activity. Psychomotor and visual function tests in man have shown that the non-sedating antihistamines do not impair psychomotor performance or adversely affect subjective feelings, in a constrast to conventional antihistamines which were active in these tests. The non-sedating antihistamines neigher affect the EEG as sedative antihistamines are known to do, nor interact with other depressant drugs (such as alcohol or benzodiazepines) to produce enhanced depressant effects.

The lack of sedative effects from the non-sedating antihistamines may be especially useful in children, where prescibing of conventional antihistamines is often hindered because of the daytime sedation they produce.

The non-sedating antihistamines include acrivastine, AHR-11325, astemizole, azatadine, azelastine, cetirizine, ebastine, ketotifen, lodoxamide, loratidine, levocabastine, maquitazine, oxatomide, setastine, tazifylline, temelastine, and terfenadine. Representative chemical structures for many of the non-sedating antihistamines are presented in Table I.

TABLE I

Non-Sedating Antihistamines

| Common Name or Generic Name | Chemical Structure | Chemical Name |
|---|---|---|
| acrivastine | 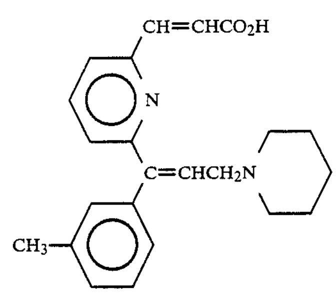 | 3-(6-(1-(4-methylphenyl)-3-(1-pyrrolidinyl)-1-propenyl)-2-pyridinyl)-2-propenoic acid |
| astemizole | 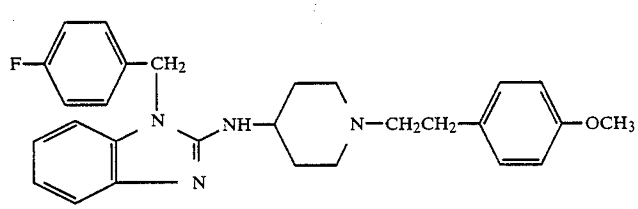 | 4-(2-(4-((1-((4-fluorophenyl)methyl)-1H-benzimidazol-2-yl)amino)-1-piperidinyl)ethyl)-phenol |
| azatadine | 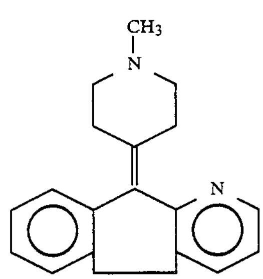 | 6,11-dihydro-11-(methyl-4-piperidinylidene)-5H-Benzo(5,6)cyclohepta(1,2-b)-pyridine [(Z)-2-butenedioate (1:2)] 6,11-dihydro-11-(1-methyl-4-piperidylidene)-5H-Benzo(5,6)cyclohepta(1,2-b)-pyridine [maleate (1:2)] |

TABLE I-continued

Non-Sedating Antihistamines

| Common Name or Generic Name | Chemical Structure | Chemical Name |
|---|---|---|
| ketotifen | 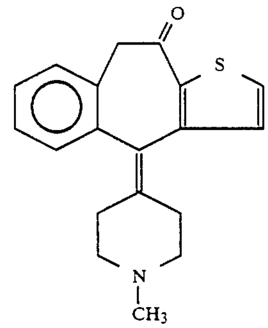 | 4,9-dihydro-4-(1-methyl-4-piperidinylidene)-10H-benzo(4,5)cyclohepta(1,2-b)-thiophen-10-one [(E)-2-butenedioate (1:1)] |
| lodoxamide | 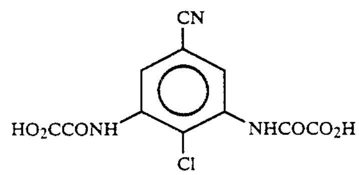 | 2,2'-((2-chloro-5-cyano-1,3-phenylene)diimino)bis(2-oxo-acetic acid) compound with 2-amino-2-(hydroxymethyl)-1,3-propanediol (1:2) |
| levocabastine | 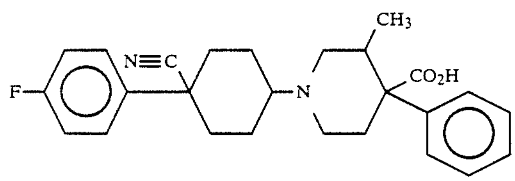 | 1-(4-cyano-4-(4-fluorophenyl)cyclohexyl)-3-methyl-4-phenyl-4-piperidinecarboxylic acid |
| mequitazine | 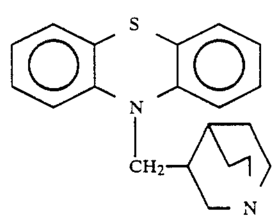 | 10-(1-azabicyclo(2.2.2)oct-3-yl-methyl)-10H-phenothiazine |
| oxatomide | 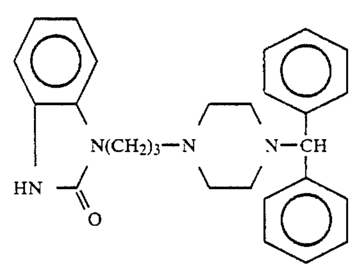 | 1-(3-(4-(diphenylmethyl)-1-piperazinyl)propyl)-1,3-dihydro-2H-benzimidazol-2-one |
| tazifylline | 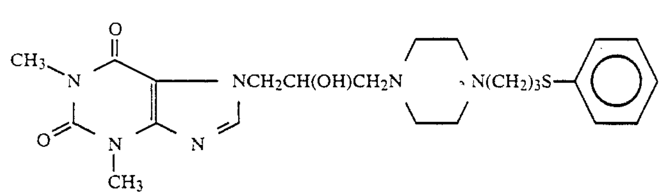 | 3,7-dihydro-7-(2-hydroxy-3-(4-(3-(phenylthio)propyl)-1-piperazinyl)propyl)-1,3-dimethyl-1H-purine-2,6-dione |

TABLE I-continued

Non-Sedating Antihistamines

| Common Name or Generic Name | Chemical Structure | Chemical Name |
|---|---|---|
| temelastine | 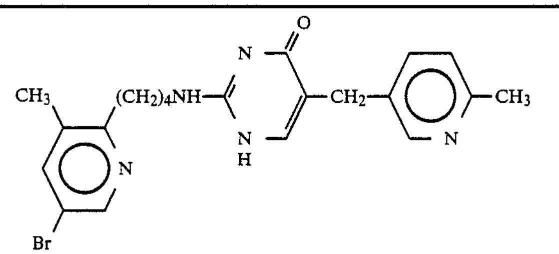 | 2-((4-(5-bromo-3-methyl-2-pyridinyl)butyl)amino)-5-((6-methyl-3-pyridinyl)methyl)-4(1H)-pyrimidinone |
| terfenadine | 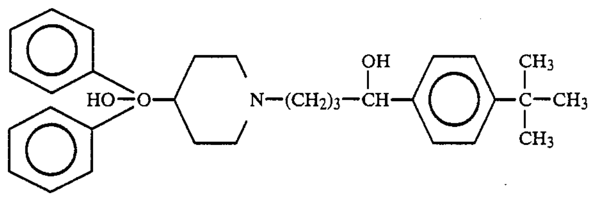 | alpha-(4-(1,1-dimethylethyl)phenyl)-4-(hydroxydiphenylmethyl)-1-piperidinebutanol |
| loratidine | 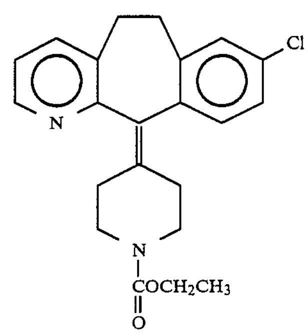 | (8-chloro(6,11-dihydro-11-(1-carboethoxy-4-piperidylidene)-5-H-benzo(5,6)cyclohepta(1,2-b]-pyridine) |

The preferred non-sedating antihistamines for use in the practice of the present invention are astemizole and terfenadine. Terfenadine is marketed in the United States as Seldane, a registered trademark of Merill Dow Pharmaceuticals.

The amount of the non-sedating antihistamine useful in the practice of the present invention generally ranges from about 1 mg to about 1000 mg depending on the specific non-sedating antihistamine selected; however, greater or lesser amounts may be employed if desired or necessary.

The recommended dosage of terfenadine, for instance, is 60 mg orally (1 tablet or 10 ml of suspension) once or twice daily. In children aged 6 to 12 years, the dosage in 30 mg (5 ml of suspensio) to 60 mg twice daily depending on body weight. In children aged 3 to 5 years, the dosage is 15 mg twice daily. Some studies suggest doses ranging from 20 mg thrice daily to 200 mg thrice daily.

The usual dose of astemizole is 10 mg to 25 mg once daily. Astemizole has a half-life of several days and thus it may be given as a single tablet daily, which is an important advantage in obtaining greater patient compliance; therefore, it can advantageously be added to one of the longer acting NSAID's. The recommended dose of mequitazine for use in the practice of the present invention is 5 mg twice daily. SL&F 93944 is being evaluated in humans at a dose of 100 mg once or twice daily.

The cough/cold pharmaceutical compositions of the present invention comprise, in addition to aspirin, sodium salicylate, salicylamine or acetaminophen at least one non-sedating antihistamine as an active ingredient and optionally one or more active ingredients from the following pharmacological classes: sympathomimetics (nasal decongestants, bronchodilators), cough suppressants-antitussives and expectorants. Typical therapeutically active components from these categories, along with their usual adult dosage, for use in the pharmaceutical compositions and methods of the invention are set forth in the following Table II. Of course, sustained release formulations would contain higher doses than those set forth in Table II.

These non-sedating antihistamines could enhance the analgesic properties of aspirin, sodium salicylate, salicylamide and acetaminophen as has been observed for conventional antihistamines when combined with the newer NSAID's. Notably, diphenhydramine, a conventional antihistamine, in combination with a non-steroidal antiinflammatory drug, ibuprofen, has already been demonstrated by Applicants to produce a synergistically enhanced analgesic response in a mammalian organism. Compare their U.S. Pat. No. 4,522,826.

TABLE II

| DRUG (FORM-SALT) | AC- TION | PREPARATIONS | USUAL SINGLE DOSE (ADULT) |
|---|---|---|---|
| pseudoephedrine (sulfate, HCl) | D | Tablet, Capsule 30 mg, 60 mg, 120 mg (sustained | 30–120 mg |

TABLE II-continued

| DRUG (FORM-SALT) | AC- TION | PREPARATIONS | USUAL SINGLE DOSE (ADULT) |
|---|---|---|---|
| phenylpropanolamine | D | action) Tablet, Capsule, Elixir, 25 mg, 50 mg, 12.5 mg/5 cc | 5-50 mg |
| phenylephrine (bitartrate, tannate, HBr, HCl) | D | Tablet, Capsule Elixir, 5 mg, 10 mg, 25 mg, 5 mg/5 cc | 5-25 mg |
| caramiphen (edisylate) | CS | Capsule, Elixir 20 mg, 5 mg/5 cc | 5-20 mg |
| dextromethorphan (HBr) | CS | Tablet, Capsule, Elixir 15 mg, 30 mg 15 mg/5 cc | 2.5-30 mg |
| codeine (phosphate, sulfate) | CS | Tablet, Elixir 10 mg 10 mg/5 cc | 10-20 mg |
| benzonatate | CS | Capsule 100 mg | 100 mg |
| chlophedianol (HCl) | CS | Elixir 25 mg/5 cc | 25 mg |
| terpin hydrate | E | Tablet, Elixir 300 mg | 85-300 mg |
| quaifenesin (glyceryl quaiacolate | E | Tablet, Capsule, Elixir, 100 mg, 100 mg/5 cc | 25-200 mg |
| potassium (Iodide) citrate) | E | Tablet, Elixir 100 mg, 100 mg/5 cc | 150-300 mg |
| potassium guaicolsulfonate | E | Elixir 80 mg/5 cc | 45-300 mg |

D = decongestant
CS = cough suppressant
E = expectorant

In the pharmaceutical compositions and methods of the present invention, the foregoing active ingredients will typically be administered in admixtures with suitable pharmaceutical diluents, excipients or carriers (collectively referred to herein as "carrier" materials) suitably selected with respect to the intended form of administration, i.e., oral tablets, capsules, elixirs, syrups, suspensions, etc. and consistent with conventional pharmaceutical practices. For instance, for oral administration in the form of tablets or capsules, the active drug components may be combined with any oral nontoxic pharmaceutically acceptable inert carrier such as lactose, starch, sucrose, cellulose, magnesium stearate, dicalcium phosphate, calcium sulfate, mannitol, ethyl alcohol (liquid forms) and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, etc. Disintegrators include, without limitation, starch, methylcellulose, agar, bentonite, guar gum, etc. Sweetening and flavoring agents and preservatives can also be included where appropriate.

Of course, additionally, the compositions of the present invention may be formulated in sustained release form to provide the rate controlled release of any one or more of the components to optimize the therapeutic effects, i.e., analgesia, antihistaminic, etc. while minimizing undesirable side effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

As representative suitable formulations consistent with the objects, features and advantages of the present invention, the following non-limiting examples are provided.

EXAMPLE 1

| Acetaminophen | 1000 mg |
|---|---|
| Dextromethorphan hydrobromide | 30 mg |
| Guaifenesin | 100 mg |
| Terfenadine | 60 mg |

Triturate active ingredients and q.s. with lactose to selected capsule size.

EXAMPLE 2

In each fluid ounce:

| Acetaminophen | 1000 mg |
|---|---|
| Dextromethorphan hydrobromide | 30 mg |
| Astemizole | 10 mg |

Orange flavoring and alcohol 10% v/v.

EXAMPLE 3

| Aspirin | 500 mg |
|---|---|
| Terfenadine | 60 mg |

Triturate active ingredients and q.s. with lactose to selected capsule size.

From the foregoing, other typical acceptable pharmaceutical formulations will be apparent to those skilled in the art of pharmaceutical formulations.

While this invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove with respect to the active ingredients may be applicable as a consequence of variations of the responsiveness of the mammal treated, severity of symptoms, dosage related adverse effects, if any, observed and similar considerations. Accordingly, such expected variations or differences in the practice of the present invention and the results obtained are contemplated in accordance with the objects and practices of the present invention. It is intended, therefore, that the invention be limited only by the scope of the claims which follow.

What is claimed is:

1. A pharmaceutical composition of matter for use in the treatment of cold symptoms, cold-like symptoms, flu symptoms, or cough or any combination thereof and the discomfort, pain, headache, fever and general malaise associated therewith, in a mammalian organism, and adapted for unit dosage oral administration, said composition comprising (i) an analgesically and anti-inflammatorily effective amount of aspirin, salicylamide or sodium salicylate, or pharmaceutically acceptable salt thereof, in combinatory immixture with (ii) an antihistaminically effective amount of at least one of the non-sedating antihistamines, acrivastine, astemizole, azatadine, cetirizine, ketotifen, loratidine, temelastine, terfenadine or pharmaceutically acceptable salt thereof.

2. The pharmaceutical composition as defined by claim 1, comprising 300 mg to 2.0 grams of component (i).

3. The pharmaceutical composition as defined by claim 1, comprising (i) an analgesically and anti-inflammatorily effective amount of aspirin.

4. The pharmaceutical composition as defined by claim 3, comprising 300 mg to 1 gram of aspirin.

5. The pharmaceutical composition as defined by claim 1, comprising (i) an analgesically and anti-inflammatorily effective amount of sodium salicylate.

6. The pharmaceutical composition as defined by claim 5, comprising 300 mg to 2.0 grams of sodium salicylate.

7. The pharmaceutical composition as defined by claim 1, comprising (i) an analgesically and anti-inflammatorily effective amount of salicylamide.

8. The pharmaceutical composition as defined by claim 7, comprising 300 mg to 2.0 grams salicylamide.

9. The pharmaceutical composition as defined by claim 1, comprising from 1 mg to 1000 mg of said non-sedating antihistamine.

10. The pharmaceutical composition as defined by claim 1, wherein said non-sedating antihistamine is terfenadine or pharmaceutically acceptable salt thereof.

11. The pharmaceutical composition as defined by claim 10, comprising 30 mg to 120 mg of terfenadine.

12. The pharmaceutical composition as defined by claim 1, wherein said non-sedating antihistamine is astemizole or pharmaceutically acceptable salt thereof.

13. The pharmaceutical composition as defined by claim 12, comprising 10 mg to 25 mg astemizole.

14. The pharmaceutical composition as defined by claim 4, comprising 30 mg to 120 mg of terfenadine.

15. The pharmaceutical composition as defined by claim 1, further comprising (iii) a pharmaceutically acceptable non-toxic carrier.

16. The pharmaceutical composition as defined by claim 1, in oral dosage form.

17. The pharmaceutical composition as defined by claim 16, in oral dosage tablet form.

18. The pharmaceutical composition as defined by claim 16, in oral dosage capsule form.

19. The pharmaceutical composition as defined by claim 16, in oral dosage suspension form.

20. The pharmaceutical composition as defined by claim 1, wherein said non-sedating antihistamine is acrivastine.

21. The pharmaceutical composition as defined by claim 1, wherein said non-sedating antihistamine is azatadine.

22. The phamaceutical composition as defined by claim 1, wherein said non-sedating antihistamine is cetirizine.

23. The pharmaceutical composition as defined by claim 1, wherein said non-sedating antihistamine is ketotifen.

24. The pharmaceutical composition as defined by claim 1, wherein said non-sedating antihistamine is loratidine.

25. The pharmaceutical composition as defined by claim 1, wherein said non-sedating antihistamine is temelastine.

26. A method for the treatment of cold symptoms, cold-like symptoms, flu symptoms, cough or any combination thereof and the discomfort, pain, headache, fever and general malaise associated therewith, in a mammalian organism in need of such treatment comprising administering to such organism a sympton relieving antihistaminically, analgesically and anti-inflammatory effective amount of a composition comprising (i) aspirin, salicylamide or sodium salicylate, or pharmaceutically acceptable salt thereof, in combinatory immixture with (ii) at least one of the non-sedating antihistamines acrivastine, astemizole, azatadine, cetirizine, ketotifen, loratidine, temelastine, terfenadine or pharmaceutically acceptable salt thereof.

27. A method for the treatment of cold symptoms, cold-like symptoms, flu symptoms, cough or any combination thereof and the discomfort, pain, headache, fever and general malaise associated therewith, in a mammalian organism in need of such treatment comprising administering to such organism the pharmaceutical composition as defined by claim 2.

28. A method for the treatment of cold symptoms, cold-like symptoms, flu symptoms, cough or any combination thereof and the discomfort, pain, headache, fever and general malaise associated therewith, in a mammalian organism in need of such treatment comprising administering to such organism the pharmaceutical composition as defined by claim 4.

29. A method for the treatment of an allergic reaction in a mammalian organism in need is such treatment, comprising administering to such organism an allergic symptom relieving effective amount of a composition comprising (i) aspiring, salicylamide or sodium salicylate or pharmaceutially acceptable salt thereof, in combinatory immixture with (ii) at least one of the non-sedating antihistamines, acrivastine, astemizole, azatadine, cetirizine, ketotifen, loratidine, temelastine, terfenadine or pharmaceutically acceptable salt thereof.

30. The method as defined by claim 29, said allergic reaction comprising coryza or rhinitis.

31. The method as defined by claim 29, wherein said non-sedating antihistamine is astemizole.

32. The method as defined by claim 29, wherein said non-sedating antihistamine is acrivastine.

33. The method as defined by claim 29, wherein said non-sedating antihistamine is terfenadine.

* * * * *